United States Patent [19]

Koguchi et al.

[11] Patent Number: 4,522,812
[45] Date of Patent: Jun. 11, 1985

[54] NOVEL PHYSIOLOGICALLY ACTIVE SUBSTANCE K-4, A PROCESS FOR PREPARATION THEREOF AND A PHARMACEUTICAL COMPOSITION CONTAINING THE SAME

[75] Inventors: Toshiro Koguchi, Yokohama; Hiroshi Kase, Koganei; Isao Kawamoto, Hiratsuka, all of Japan; Masaji Kasai, Rockville, Md.; Kunikatsu Shirahata, Komae, Japan; Ryo Okachi, Shizuoka, Japan; Kiyoshi Nakayama, Sagamihara, Japan

[73] Assignee: Kyowa Hakko Kogyo Co., Ltd., Tokyo, Japan

[21] Appl. No.: 407,082

[22] Filed: Aug. 11, 1982

[30] Foreign Application Priority Data

Aug. 18, 1981 [JP] Japan ............................. 56-128740

[51] Int. Cl.³ ..................... C07C 103/52; A61K 37/02
[52] U.S. Cl. ................................ 514/7; 260/112.5 R
[58] Field of Search ................ 260/112.5 R; 424/177

[56] References Cited

U.S. PATENT DOCUMENTS

| | | | |
|---|---|---|---|
| 4,016,148 | 4/1977 | Antherton et al. | 424/177 |
| 4,100,275 | 7/1978 | Antherton et al. | 424/177 |
| 4,127,649 | 11/1978 | Antherton et al. | 424/271 |
| 4,134,972 | 1/1979 | Antherton et al. | 424/271 |
| 4,213,969 | 7/1980 | Baylis | 424/177 |
| 4,250,085 | 2/1981 | Antherton et al. | 260/112.5 R |
| 4,331,591 | 5/1982 | Baylis | 260/112.5 R |

Primary Examiner—Delbert R. Phillips
Assistant Examiner—F. T. Moezie
Attorney, Agent, or Firm—Fitzpatrick, Cella, Harper & Scinto

[57] ABSTRACT

Disclosed is a novel physiologically active substance K-4 which has a hypotensive activity, a process production thereof and a pharmaceutical composition containing the same.

2 Claims, 4 Drawing Figures

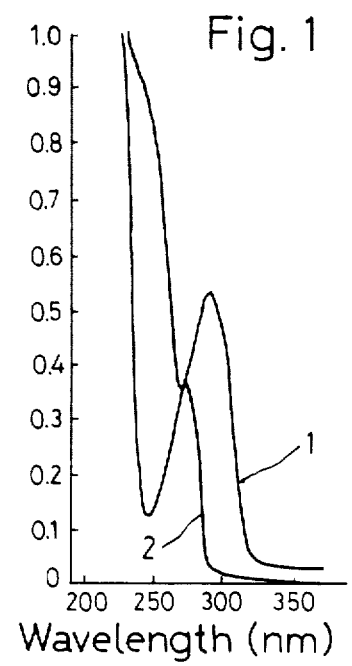
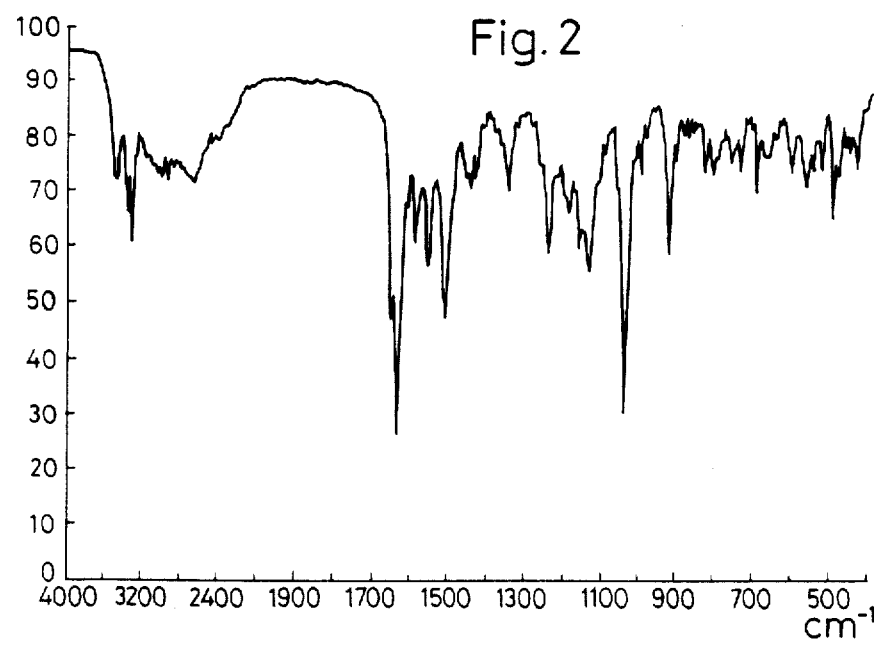

NOVEL PHYSIOLOGICALLY ACTIVE SUBSTANCE K-4, A PROCESS FOR PREPARATION THEREOF AND A PHARMACEUTICAL COMPOSITION CONTAINING THE SAME

RELATED APPLICATIONS

The present invention is related generally to the invention disclosed in U.S. Patent Application Ser. No. 359,030 filed Mar. 17, 1982 for Novel Physiologically Active Substance K-26, A Process for Production Thereof and A Pharmaceutical Composition Containing the Same.

BACKGROUND OF THE INVENTION

The present invention relates to a novel physiologically active substance and a process for producing the same. New physiologically active substances useful as medicaments or their intermediates are always in demand. To this end, it has been found that a new physiologically active substance is produced in the culture liquor of a microorganism belonging to the genus Actinomadura. When isolated and purified, the substance exhibits marked hypotensive activity. The substance has been named K-4 and its properties, a process for producing the same and a pharmaceutical composition containing the same are described hereinafter.

SUMMARY OF THE INVENTION

In accordance with the present invention, K-4 is produced by culturing a K-4 producing strain of a microorganism belonging to the genus Actinomadura in a nutrient medium unit recoverable amounts of K-4 are formed in the culture liquor and thereafter isolating K-4 therefrom.

According to the composition of matter aspects of the invention a novel physiologically active substance exhibiting hypotensive activity is represented by the formula:

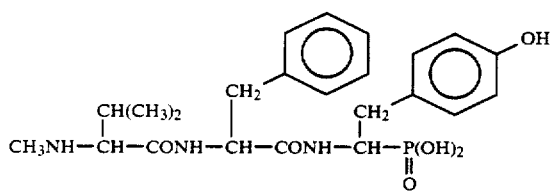

Finally, the present invention pertains to pharmaceutical compositions comprising an effective hypotensive amount of the compound, K-4 along with pharmacologically acceptable excipients.

BRIEF DESCRIPTION OF DRAWINGS

FIG. 1 is an ultraviolet absorption spectrum of K-4, where curve (1) illustrates the spectrum of K-4 in 0.1N aqueous sodium hydroxide and curve (2) illustrates the spectrum in 0.1N hydrochloric acid (concentration: 200 μg/ml).

FIG. 2 is an infrared absorption spectrum of K-4.

DETAILED DESCRIPTION OF THE INVENTION

Figure 3:
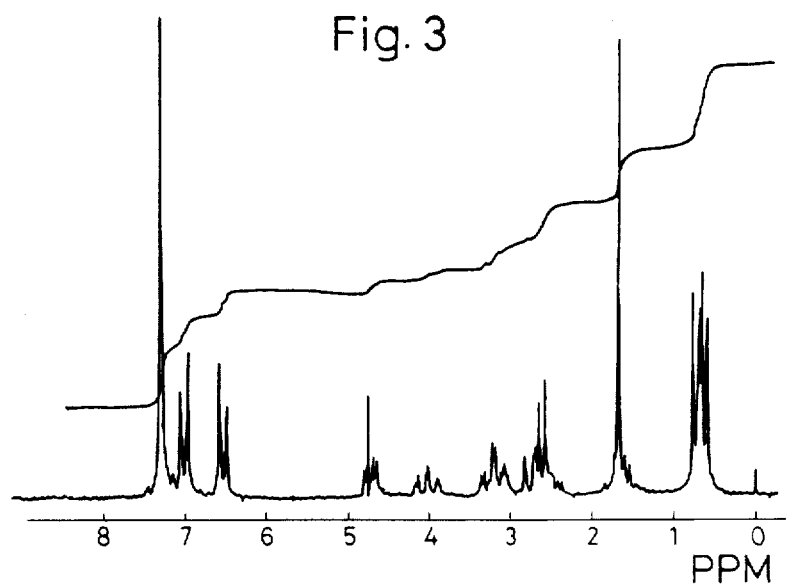
FIG. 3 is a PMR spectrum of K-4.

For the production of the present physiologically active substance, microorganisms belonging to the genus Actinomadura are used. An example of a suitable strain is a strain K-4 isolated by the present inventors from a soil sample in Kagoshima City in Kagoshima Prefecture, Japan.

The morphological, cultural and physiological characteristics of the strain, determined according to the procedure described by Searing et al. in Intern. J. System. Bacteriol 16 313–340 (1966) are as follows:

I. Morphological characteristics

The K-4 strain grows very poorly on a chemically defined medium such as glucose-asparagine agar medium, starch-inorganic salt agar medium, etc. but grows vigorously on a natural nutrient medium such as yeast extract-malt extract agar medium, glucose-yeast extract agar medium, etc. with good formation of white aerial mycelia. Substrate mycelium is relatively short, branched, 0.4–0.6 μm in diameter, and sometimes fragmented at tip ends. Aerial mycelium is well developed, branched and 0.6–0.8 μm in diameter.

Chains of up to 10 spores, which are hooked or spiral, are borne on the sporophores simply branched from the aerial mycelia, and sometimes are tightly closed forming pseudosporangia. The spores are oval in shape, 0.6–0.7 μm × 0.8–1.0 μm in a size, spiny surfaced and have no flagella. No formation of sporangiospore, sclerotium, etc. are observed.

II. Growth on Various Media

The growth and color characteristics when the K-4 strain is cultured on various culture media at 28° C. for 2 weeks are given below. Color identification is made in accordance with the color classification of "Color Harmony Manual" (Container Corporation of America). No soluble pigment is observed on all the media used.

1. Glucose-asparagine agar medium
   Growth: very poor
2. Glycerol-asparagine agar medium
   Growth: very poor
3. Starch-inorganic salt agar medium
   Growth: very poor
4. Egg-albumin medium
   Growth: very poor
5. Sucrose-nitrate agar medium
   Growth: poor
   Reverse color: light ivory (2 ca)
   Aerial mycelium: poor, pearl shell tint (3 ba)
6. Glycerol-calcium maleate agar medium
   Growth: poor
   Reverse color: colorless
   Aerial mycelium: very poor, white (a)
7. Nutrient agar medium
   Growth: moderate
   Reverse color: amber (3 lc)
   Aerial mycelium: none
8. Yeast extract-malt extract agar medium
   Growth: good
   Reverse color: light amber (3ic)
   Aerial mycelium: moderate to abundant, white (a)
9. Oatmeal agar medium
   Growth: moderate
   Reverse color: light wheat (2 ea)
   Aerial mycelium: very poor, white (a)

10. Bennet's agar medium
   Growth: moderate
   Reverse color: gold (2 ic)
   Aerial mycelium: moderate, white (a)
11. Emerson's agar medium
   Growth: good
   Reverse color: amber (3 nc)
   Aerial mycelium: poor, white (a)
12. Glucose-yeast extract agar medium
   Growth: good
   Reverse color: amber (3 nc)
   Aerial mycelium: abundant, white (a)
13. Hickey-Tresner's agar medium
   Growth: good
   Reverse color: gold (2 ne)
   Aerial mycelium: abundant, white (a)
14. Peptone-yeast extract-iron agar medium
   Growth: poor
   Reverse color: amber (3 nc)
   Aerial mycelium: none
15. Tyrosine agar medium
   Growth: poor
   Reverse color: light ivory (2 ca)
   Aerial mycelium: very poor, white (a)

III. Physiological properties

To determine the physiological properties, the K-4 strain is cultured at 28° C. for 2 weeks except for the determination of optimum temperature and action upon gelatin, milk and cellulose. The optimum temperature is determined after 5 days of culturing and actions upon milk, gelatin and cellulose are observed after culturing at 28° C. for one month. The present strain grows poorly on the inorganic medium of Pridham-Gottlieb (ISP No. 9). Therefore, the test for utilization of carbon source is carried out on Ludemann's medium (N.Y. Acad. Sci. 33 207, 1971).

1. Utilization of carbon source: L-and D-arabinose, D-xylose, D-glucose, D-fructose, L-rhamnose, D-galactose, sucrose, mannose, ribose, starch, and D-mannitol are utilized. Raffinose, melizitose, and glycerol are not utilized. Melibiose, inositol, and lactose are slightly utilized.
2. Liquefaction of gelatin: negative
3. Action upon milk: neither coagulation nor liquefaction
4. Decomposition of cellulose: weakly positive
5. Hydrolysis of starch: positive
6. Optimum growth pH: 6.5-7.8
7. Optimum growth temperature: 28° C.-37° C.
8. Formation of tyrosinase: negative
9. Formation of melanoid pigment: negative IV. Cell Wall Composition The cell wall of the K-4 strain contains the amino acids meso-diaminopimelic acid, alanine, and glutamic acid. Neither LL-diaminopimelic acid nor glycine are found. On the other hand, by analysis of sugars in the whole cells according to the method of Lechevalier et al. (The Actinomycetales, Gustav Fisher Verlag, Jena, 311-316, 1970), ribose, glucose, galactose, madurose, etc. are detected, but neither arabinose nor xylose is detected. According to the classification of Lechevalier et al. (Intern. J. System. Bacteriol. 20 435-443, 1970), the K-4 strain has cell walls of type III and the type B whole cell sugar pattern.

The present strain is thus classified into the genus Actinomadura of actinomycetes, in view of the spore chain formed on the aerial mycelim and the type of cell wall, etc.

Many strains of the genus Actinomadura have been recently reported. The present strain is compared with twenty-four strains in the approved list of bacterial names (Intern. J. System. Bacteriol. 30 225-420, 1980) and particularly with those which produce yellow substrate mycelia, white aerial mycelia, spores with spiny surfaces, and fail to produce soluble pigment. The present strain is considerably different from all the strains except *Actinomadura cremea.* However, *Actinomadura cremea* is reported to have spores with a rough surface, but the spores of the present strain have a spiny surface. Therefore, these two strains are different from each other. Thus, the K-4 strain is designated as *Actinomadura spiculosospora* nov. sp. K-4, and has been deposited as FERM P-6101 with the Fermentation Research Institute of Agency of Industrial Science and Technology, Japan. As a biologically pure culture, the strain is capable of producing the substance, K-4, in recoverable quantities.

As is the case with other strains of Actinomycetes, the present strain can be mutated by various mutational treatments such as ultraviolet irradiation, $Co^{60}$ irradiation, X-ray irradiation and treatment by various mutagents and all such strains having the ability to produce the K-4 substance, even though thus mutated, can be used in the present invention.

Ordinary procedures for culturing Actinomycetes may be employed for culturing the present K-4 producing strains.

Either a synthetic medium or a natural medium may be used so long as it contains suitable carbon source(s), nitrogen source(s), inorganic salt(s), etc. As the carbon source, glucose, starch, mannose, fructose, sucrose, molasses, etc. are used alone or in combination. Hydrocarbons, alcohols, organic acids, etc. can also be used, depending upon the assimilability of the microorganisms. As nitrogen sources, inorganic or organic nitrogen-containing compounds such as ammonium chloride, ammonium sulfate, urea, ammonium nitrate and sodium nitrate may be used as well as natural nitrogen sources such as peptone, meat extract, yeast extract, dry yeast, corn steep liquor, soybean meal, casamino acid and soluble vegetable protein. As inorganic salts, sodium chloride, potassium chloride, calcium carbonate, phosphates, etc. can be added to the medium. Organic or inorganic substances capable of promoting the growth of the present strains or production of K-4 can be added thereto, if desired.

A liquid culturing method, particularly a submerged stirring culture method is most suitable for culturing strains of the present invention. Culturing is desirably carried out at a temperature of 25°-40° C. and at a pH of around neutrality. K-4 is formed and accumulated in the culture liquor usually after 3-5 days of liquid culturing. When the accumulation in the culture liquor reaches a maximum, culturing is discontinued and the desired substance is isolated and purified from the filtrate of the culture liquor obtained by filtering off the cell bodies.

Ordinary procedures for isolating metabolic products of microorganisms from a culture liquor filtrate may be used for isolation and purification of K-4. That is, such procedures as adsorption and desorption by active carbon, Diaion HP-10 (adsorption resin made by Mitsubishi Kasei Kogyo Co., Ltd., Japan), etc., column chromatography by various anion exchange resins, cellulose column chromatography, silica gel column chromatography, QAE-Sephadex column chromatography, DEAE-Sephadex A-25 column chromatography, Sephadex LH-20 column chromatography (QAE-Sephadex, DEAE-Sephadex A-25 and Sephadex LH-20 are molecular sieves made by Pharmacia Fine Chemicals Inc., Sweden), and the like can be used in a proper combination.

As an example of an isolation and purification procedure, the culture liquor filtrate is adjusted to pH 7 with hydrochloric acid and then passed through a column of Diaion HP-10. The resin is washed with water and eluted with aqueous 50% (V/V) methanol. Fractions containing K-4 are collected, concentrated under reduced pressure and then freeze-dried, whereby a crude powder is obtained. The crude powder is placed on a column of cellulose powder suspended in aqueous 70% (V/V) isopropanol and eluted with the same solvent. Fractions containing K-4 are collected and concentrated under reduced pressure to remove isopropanol, and the pH is adjusted to 7.5 with diluted aqueous sodium hydroxide. The resulting solution is charged onto a column of DEAE-Sephadex A-25 equilibrated with 0.01M phosphate buffer (pH 7.5). The column is washed with the same buffer, and then elution is carried out with 0.5M phosphate buffer (pH 7.5). Fractions containing K-4 are collected and passed through a column of Diaion HP-10. The column is washed with water and elution is carried out with aqueous 50% (V/V) methanol. Fractions containing K-4 are allowed to stand in a cold room (4° C.), whereby a fine crystalline powder of K-4 is deposited. In the foregoing purification process, K-4 is detected with Rydon-Smith or iodine reaction.

The physical and chemical properties of K-4 thus obtained are as follows:

State: white, finely crystalline powder

Specific rotation: $[\alpha]_D^{20} = -83°$ C. (c=0.1, 0.1N NaOH)

Melting point: no distinct melting point is shown up to 300° C.

Solubility in solvents: soluble in aqueous 0.1N sodium hydrochloride; sparingly soluble in water and methanol; insoluble in chloroform and n-hexane.

Color reaction: positive to Rydon-Smith reaction, iodine reaction, and ninhydrin reaction and negative to Ehrlich reaction.

Constituent amino acids: K-4 is hydrolyzed in 6N hydrochloric acid at 110° C. for 20 hours and the resulting mixture is analyzed by an amino acid automatic analyzer, whereby phenylalanine and an unidentified ninhydrin reaction-positive substance are detected. Separately, a solution of K-4 in 20% hydrochloric acid is stirred at 110° C. for 21 hours and then concentrated under reduced pressure. The residue is chromatographed on a column of silica gel (developing solvent: n-butanol:acetic acid:water=4:1:1) to give phenylalanine, N-methylvaline and the aforesaid ninhydrin reaction-positive substance.

(1) The absolute configuration of the phenylalanine thus obtained is determined as follows according to the method reported in M. Hasegawa et al., Analytical Biochemistry, 63, 308 (1975).

The phenylalanine thus obtained is reacted with l-menthol in the presence of dried hydrogen chloride to form an l-menthyl ester, which is treated with trifluoroacetic anhydride to protect the amino group with a trifluoroacetyl group and analyzed by gas chromatography. The above procedure is repeated using an authentic sample of D-phenylalanine and L-phenylalanine. By comparison, the phenylalanine from K-4 is identified as L-phenylalanine.

(2) N-methylvaline contained in K-4 racemizes in hydrolysis, and the absolute configuration of the N-methylvaline is not determinable. Its absolute configuration is determined to have L-form by total synthesis of K-4.

(3) The unidentified ninhydrin reaction-positive substance thus obtained is determined to be (-)-1-amino-2-(4-hydroxyphenyl) ethylphosphonic acid (hereinafter referred to as tyrosine-P) based on its $^1$HNMR, $^{13}$CNMR, $^{31}$PNMR, mass spectrum and specific rotation.

Hydrazine decomposition: Tyrosine-P is detected by C-terminal analysis according to the hydrazine decomposition method.

Additional analysis of K-4 shows:

Ultraviolet absorption spectrum: As is illustrated in FIG. 1

Infrared absorption spectrum: As is illustrated in FIG. 2

PMR spectrum: As is illustrated in FIG. 3

Figure 4:
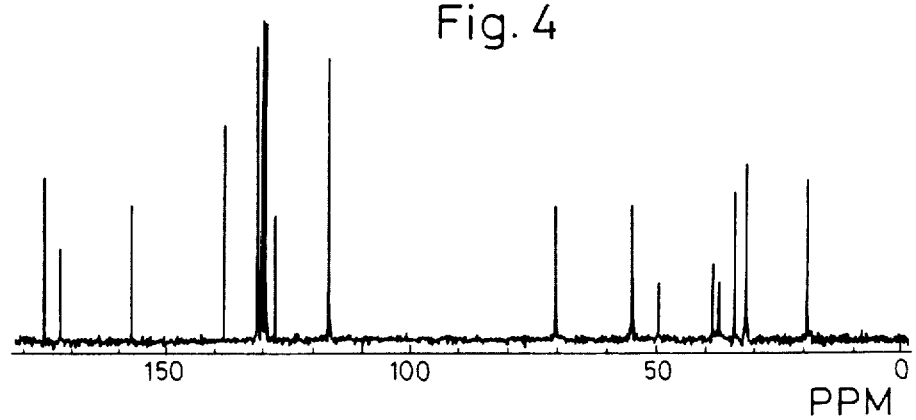
FIG. 4 is a $^{13}$C-NMR spectrum of K-4.

$^{13}$C-NMR spectrum: As is illustrated in FIG. 4

Mass spectrum: Mass spectrum of the pentatrimethylsilyl derivative obtained by treating K-4 with bis-trimethylsilyltrifluoroacetamide and pyridine shows M+ =m/Z 837.

From the foregoing physical and chemical properties, the structure of K-4 is determined to be:

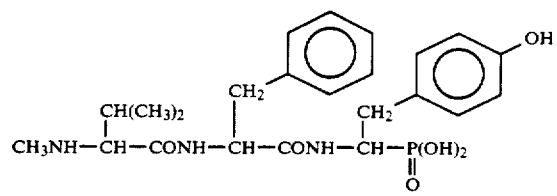

wherein the configuration of the phenylalanine and N-methylvaline parts is L-form and the tyrosine-P part has negative specific rotation.

The Rf values of K-4 on thin layer chromatography by various developing solvents are shown in Table 1 wherein the detection is carried out by Rydon-Smith reaction.

TABLE 1

| K-4 thin layer chromatography | |
|---|---|
| Developing solvent | Rf value |
| 1. n-butanol:acetic acid:water (4:1:1 V/V) | 0.37 |
| 2. aqueous 70% (V/V) isopropanol | 0.39 |
| 3. upper layer of n-butanol: n-propanol:water (2:1:3 V/V) | 0.18 |
| Thin layer Development | silica gel (Merck Art 5721) room temperature, ascending method, 4 hours |

The Rf values on thin layer chromatography of the ninhydrin reaction-positive substance produced by hydrolysis of K-4 with acid and representative amino acids are shown in Table 2.

TABLE 2

Thin layer chromatography of unidentified ninhydrin reaction-positive substance

| Amino acid | Rf value |
| --- | --- |
| 1. Phenylalanine | 0.68 |
| 2. Isoleucine | 0.73 |
| 3. Tyrosine | 0.42 |
| 4. Unidentified ninhydrin reaction-positive substance | 0.33 |

| | |
| --- | --- |
| Thin layer | Abicel SF (made by Funakoshi Yakuhin Co., Ltd., Japan) |
| Developer | n-butanol:acetic acid:water 4:1:1 (V/V) |
| Development | room temperature, ascending method, 5 hours |
| Detection | ninhydrin reaction |

The following experiment was carried out to illustrate the hypotensive activity of K-4.

Experiment

Assessment of hypotensive activity in rats implanted with a catheter:

This experiment is carried out according to the procedure described in "Evaluation of pharmacological effect (1), pharmacological test procedure (II) (Basic Lectures on Development of Drugs V)" compiled by Kyosuke Tsuda et al. and published by Chibun Shokan Publishing Co., on Oct. 10, 1971, pages 464-468.

As test animals, three male spontaneously hypertensive rats (SHR) (weight: 300-400 g) are employed in each group. The rats are intraperitoneally anesthetized with 600 mg/kg of urethane and 60 mg/kg of α-chloralose. The trachea is cannulated, and the blood pressure is recorded on an ink oscillograph through a pressure transducer (Nihon Koden MPU-0.5 made by Nihon Koden Co., Ltd.) from a polyethylene cannula inserted in a left common carotid artery.

The test compound is dissolved in physiological saline solution to yield a dosage of 0.1 ml/100 g, and intravenously administered through a cannula inserted in a left femoral vein, and the alteration of blood pressure is measured.

Changes in mean blood pressure are shown in Table 3. The mean blood pressure of 3 rats just before the administration is 142.5±20.0 mm Hg (average value ± standard error).

TABLE 3

| Sample | Dosage (mg/kg, iv) | Before administration | Blood pressure change after administration (mm Hg) | | | |
| --- | --- | --- | --- | --- | --- | --- |
| | | | 10 min. | 30 min. | 60 min. | 120 min. |
| K-4 | 100 | 0 | −15 | −22 | −35 | −5 |

As is evident from the foregoing results K-4 exhibits marked hypotensive activity.

In view of its hypotensive activity, K-4 may be used as a hypotensive agent in mammals in various formulations for administration. Pharmaceutical compositions of the present invention are prepared by uniformly mixing an effective amount of K-4 with pharmacologically acceptable excipient(s). According to formulations suitable for administration, the excipient may take various forms. It is preferred that the pharmaceutical compositions are administered by injection.

In preparation of the compositions for injection, K-4 is dissolved in an alkaline solution such as 0.1N aqueous sodium hydroxide, and the solution is adjusted to a suitable pH with an acid such as 0.1N hydrochloric acid and diluted with water to a defined volume to prepare an injection. Solubilizing agent(s) may also be used in preparation of an injection, especially an injection of low pH. Such solubilizing agents include surfactants such as hydrogenated polyoxyethylene castor oil; injectable solvents such as propylene glycol, N,N-dimethylacetamide and ethanol. Based upon the experimental data, it is expected that K-4 may be utilized as an hypotensive agent in humans. For such purposes, the active ingredient would be administered by injection in a dose of 18-75 mg per day for an adult patient (body weight: 50 kg).

Certain specific embodiments of the invention are illustrated by the following representative examples.

EXAMPLE 1

In this example, *Actinomadura spiculosospora* nov. sp. K-4 (FERM P-6101) is used as the seed strain and, as a first seed medium, a medium containing 1 g/dl glucose, 1 g/dl soluble starch, 0.3 g/dl beef extract, 0.5 g/dl yeast extract, 0.5 g/dl bactotryptone, and 0.2 g/dl calcium carbonate (pH 7.2 before sterilization) is employed. One loopful of the seed strain is inoculated in 10 ml of the seed medium in a 50 ml-large test tube, and cultured with shaking at 30° for 5 days. Three milliliters of the seed culture liquor is then added to 30 ml of a second seed medium in an 300 ml-Erlenmeyer flask. The composition of the second seed medium is the same as that of the first seed medium. Second seed culturing is carried out with shaking at 30° for 2 days. Thereafter 30 ml of the seed culture liquor is added to 300 ml of a third seed medium in a 2 l-Erlenmeyer flask with baffles. The composition of the third seed medium is the same as that of the first seed medium. The third seed culturing is carried out with shaking at 30° C. for 3 days. Then, 0.9 l (corresponding to the volume of three flasks) of the third seed culture liquor is added to 15 l of main fermentation medium in a 30 l-stainless steel jar fermenter. The main fermentation medium contains 4 g/dl soluble starch, 3 g/dl soybean meal, 0.5 g/dl corn steep liquor, 0.05 g/dl dipotassium hydrogen phosphate, 0.05 g/dl magnesium sulfate (heptahydrate), 0.03 g/dl potassium chloride, and 0.3 g/dl calcium carbonate (pH 7.8 before sterilization). The main fermentation is carried out at 30° C. for 5 days with aeration (15 l/min) and agitation (300 r.p.m.). The thus obtained culture liquor is then admixed with about 1 kg of filter aid, Radiolite No. 600 (made by Showa Kagaku Kogyo Co., ltd. Japan), and filtered under reduced pressure to obtain 14 l of filtrate. The filtrate is adjusted to pH 7.0 with hydrochloric acid, and passed through a column of 1 l of Diaion HP-10. The column is washed with water and eluted with aqueous 50% (V/V) methanol. Fractions containing K-4 are concentrated under reduced pressure to remove methanol and then freeze-dried to obtain 13.0 g of crude brown powder. The 13.0 g of the thus obtained crude K-4 powder is placed on a column of about 1 l of Abicel (cellulose made by Funakoshi Yakuhin Co., Ltd., Japan) which is suspended in aqueous 70% (V/V) isopropanol and charged onto the column uniformly in advance. Elution is then carried out with the same solvent. Fractions containing K-4 are collected and concentrated under reduced pressure to remove isopropanol. The thus obtained concentrated solution is adjusted to pH 7.5 with sodium hydroxide. The concentrated solution is charged onto a column of 500 ml of DEAE-Sephadex A-25 equilibrated with 0.01M phosphate buffer (pH 7.5) in advance. Then, the column is washed with the same buffer, and elution is carried out with 0.5M phosphate buffer (pH 7.5).

Fractions containing K-4 are collected and adjusted to pH 7.0 with hydrochloric acid, and then passed through a column of 100 ml of Diaion HP-10. The column is washed with water and elution is carried out with aqueous 50% (V/V) methanol. Fractions containing K-4 are allowed to stand in a cold room (4° C.), whereby 6.5 mg of a finely crystalline white powder of K-4 is deposited and recovered.

The thus obtained K-4 has the physical and chemical properties as given above.

In the foregoing process, detection of K-4 is carried out by means of Rydon-Smith or iodine reaction.

EXAMPLE 2

Five hundred milligrams of K-4 is dissolved in 0.1N aqueous sodium hydroxide, and the solution is adjusted to pH 9 with 0.1N hydrochloric acid and diluted to a volume of 20 ml with water. The solution is filtered under sterile condition with a membrane filter. The filtrate is poured in an ampule by portions of 5 ml. The ampule is sealed and sterilized at 121° C. for 20 minutes with high pressure steam to prepare an injection.

EXAMPLE 3

One hundred milligrams of K-4 and 500 mg of surfactant, HCO-60 (made by Nikko Chemicals Co., Ltd., Japan) are dissolved in water. The solution is diluted to a volume of 20 ml with water. The resulting solution is treated in the same manner as in Example 7 to prepare an injection containing 50 mg of K-4 per ampule (10 ml).

What is claimed is:

1. The compound, K-4, represented by the formula

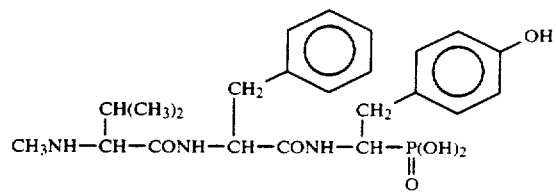

wherein the configuration of the phenylalanine and N-methylvaline parts is L-form and the 1-amino-2-(4-hydroxyphenyl) ethylphosphonic acid part has negative specific rotation.

2. A hypotensive pharmaceutical composition which comprises an effective amount of the compound of claim 1 and at least one pharmacologically acceptable excipient.

UNITED STATES PATENT AND TRADEMARK OFFICE
CERTIFICATE OF CORRECTION

PATENT NO. : 4,522,812

DATED : June 11, 1985

INVENTOR(S) : TOSHIRO KOGUCHI, et al.

It is certified that error appears in the above-identified patent and that said Letters Patent is hereby corrected as shown below:

Cover Page, at [30] under "Foreign Application Priority Data", "Aug. 18, 1981" should read --Aug. 19, 1981--.

Signed and Sealed this

Fifteenth Day of October 1985

[SEAL]

Attest:

DONALD J. QUIGG

Attesting Officer

Commissioner of Patents and
Trademarks—Designate